(12) United States Patent
Fujimori et al.

(10) Patent No.: US 8,246,537 B2
(45) Date of Patent: Aug. 21, 2012

(54) CAPSULAR ENDOSCOPE

(75) Inventors: Noriyuki Fujimori, Suwa (JP);
Masanori Ogata, Matsumoto (JP);
Kenji Miyata, Okaya (JP)

(73) Assignee: Olympus Corporation, Tokyo (JP)

( * ) Notice: Subject to any disclaimer, the term of this patent is extended or adjusted under 35 U.S.C. 154(b) by 1278 days.

(21) Appl. No.: 11/961,740

(22) Filed: Dec. 20, 2007

(65) Prior Publication Data
US 2008/0114204 A1    May 15, 2008

Related U.S. Application Data

(62) Division of application No. 10/900,809, filed on Jul. 28, 2004, now abandoned.

(30) Foreign Application Priority Data

Aug. 4, 2003  (JP) ................................. 2003286091

(51) Int. Cl.
*A61B 1/06* (2006.01)
(52) U.S. Cl. ...................................... 600/160
(58) Field of Classification Search ................. 600/109, 600/117–118, 160, 302
See application file for complete search history.

(56) References Cited

U.S. PATENT DOCUMENTS

| | | | |
|---|---|---|---|
| 5,607,435 A | | 3/1997 | Sachdeva et al. |
| 5,653,677 A | * | 8/1997 | Okada et al. ................... 600/112 |
| 5,766,189 A | | 6/1998 | Matsuno |
| 5,819,736 A | * | 10/1998 | Avny et al. ..................... 600/407 |
| 5,993,378 A | | 11/1999 | Lemelson |
| 6,662,041 B2 | | 12/2003 | Burbank et al. |
| 2001/0049539 A1 | | 12/2001 | Rehil |
| 2001/0051766 A1 | * | 12/2001 | Gazdzinski ................... 600/309 |
| 2003/0020810 A1 | * | 1/2003 | Takizawa et al. ............... 348/68 |
| 2003/0023150 A1 | * | 1/2003 | Yokoi et al. ................... 600/300 |
| 2003/0060702 A1 | | 3/2003 | Kuth et al. |
| 2003/0167000 A1 | | 9/2003 | Mullick et al. |
| 2003/0199826 A1 | | 10/2003 | Windheuser et al. |
| 2003/0214580 A1 | | 11/2003 | Iddan |
| 2004/0092825 A1 | | 5/2004 | Madar et al. |
| 2004/0162465 A1 | | 8/2004 | Carrillo |
| 2004/0225188 A1 | | 11/2004 | Kleen et al. |

FOREIGN PATENT DOCUMENTS

| | | |
|---|---|---|
| DE | 103 17 368 A1 | 12/2004 |
| JP | 58-81022 | 5/1983 |
| JP | 4-102450 | 4/1992 |
| JP | 9-192135 | 7/1997 |
| JP | 10-099770 | 4/1998 |
| JP | 2001-46357 | 2/2001 |
| JP | 2002-556 | 1/2002 |
| JP | 2003-111720 | 4/2003 |
| JP | 2003-210395 | 7/2003 |
| JP | 2003-524448 | 8/2003 |
| JP | 2004-135902 | 5/2004 |
| WO | WO 00/22975 | 4/2000 |
| WO | WO 03/005877 A2 | 1/2003 |

* cited by examiner

*Primary Examiner* — Philip R Smith
(74) *Attorney, Agent, or Firm* — Scully, Scott, Murphy & Presser, P.C.

(57) ABSTRACT

According to the present invention, a capsular endoscope having at least an image pickup optical system, an illumination unit, an image pickup portion, and a circuit board comprises a marker shooting unit that indwells a marker member in a body cavity. Consequently, a predetermined marker is indwelled in a desired region such as a lesion discovered using the capsular endoscope so that the region can be readily rediscovered during reexamination.

11 Claims, 8 Drawing Sheets

CAPSULAR ENDOSCOPE

This application is a divisional application of co-pending U.S. application Ser. No. 10/900,809 filed on Jul. 28, 2004 which claims the benefit of Japanese Application No. 2003-286091 filed on Aug. 4, 2003, the contents of each of which are incorporated herein by this reference.

BACKGROUND OF THE INVENTION

1. Field of the Invention

The present invention relates to a capsular endoscope, or more particularly, to a capsular endoscope having an image pickup optical system, image pickup means, and others integrated into a substantially capsule-shaped housing.

2. Description of the Related Art

In the past, endoscope systems have been used in practice and widely adopted for examination or the like of, for example, body cavities. The endoscope system comprises a tubular insertional unit having an image pickup device incorporated in the distal part thereof, an operating unit coupled to the insertional unit, and various pieces of equipment connected to the operating unit including an image processing unit, a display device, and a light source unit or the like. The insertional unit is inserted into a body cavity through a subject's oral cavity or the like in order to observe a desired region in the body cavity. In the conventional endoscope device, a range that can be observed or examined is limited due to restrictions including a restriction on the length of the insertional unit to be inserted into a body cavity.

In recent years, various proposals have been made of a capsular endoscope system comprising: a so-called capsular endoscope that is a compact endoscope having image pickup means which includes an image pickup optical system, illuminating means, communicating means, and power receiving means or a power supply incorporated in a capsule-shaped housing; communicating means for communicating with the capsular endoscope by radio; recording means for recording a received signal; and display means for displaying the received signal on a CRT or an LCD or the like.

When a conventional capsular endoscope is used to examine an intracavitary region, if a lesion or the like is discovered in the subject's body cavity, close examination may be performed using a general-purpose endoscope or the like or predetermined treatment may be performed in addition to the close examination.

In such a case, if accurate positional information representing the position of the lesion discovered through the preceding examination performed using the capsular endoscope were acquired, the lesion would be easily rediscovered during the close examination such as endoscopic examination to be performed later.

Accordingly, various proposals have been made of means for detecting the position of a conventionally proposed capsular endoscope that has been inserted into a body cavity for the purpose of examination and diagnosis. For example, Japanese Unexamined Patent Application Publication No. 2001-46357 has proposed such means.

In a capsular endoscope system disclosed in the Japanese Unexamined Patent Application Publication No. 2001-46357, position detecting means for detecting the position of the capsular endoscope that has been inserted into a body cavity is incorporated in an external receiving device. The position detecting means receives a predetermined signal originating from the capsular endoscope lying in the body cavity, and acquires information on the position of the capsular endoscope in the body cavity on the basis of the strength of the predetermined signal.

However, the position detecting means disclosed in the Japanese Unexamined Patent Application Publication No. 2001-46357 cannot presumably detect the position with satisfactory precision because the signal sent from the capsular endoscope lying in a body cavity is feeble.

Consequently, when close examination or the like is performed later, an operator has to perform labor-intensive work of rediscovering a lesion that is an object of examination and that has been discovered through the previous examination performed using the capsular endoscope.

As mentioned above, when the capsular endoscope is used for examination, if positional information on a lesion discovered through the examination is acquired, the positional information will prove quite helpful. Provision of high-precision positional information is therefore demanded.

SUMMARY OF THE INVENTION

According to the present invention, a capsular endoscope comprises at least an image pickup optical system, illuminating means, image pickup means, and a circuit board. The capsular endoscope further comprises marking means for indwelling a marker member in a body cavity.

The advantages of the present invention will be apparent from the description made below.

DESCRIPTION OF THE PREFERRED EMBODIMENTS

Figure 1:
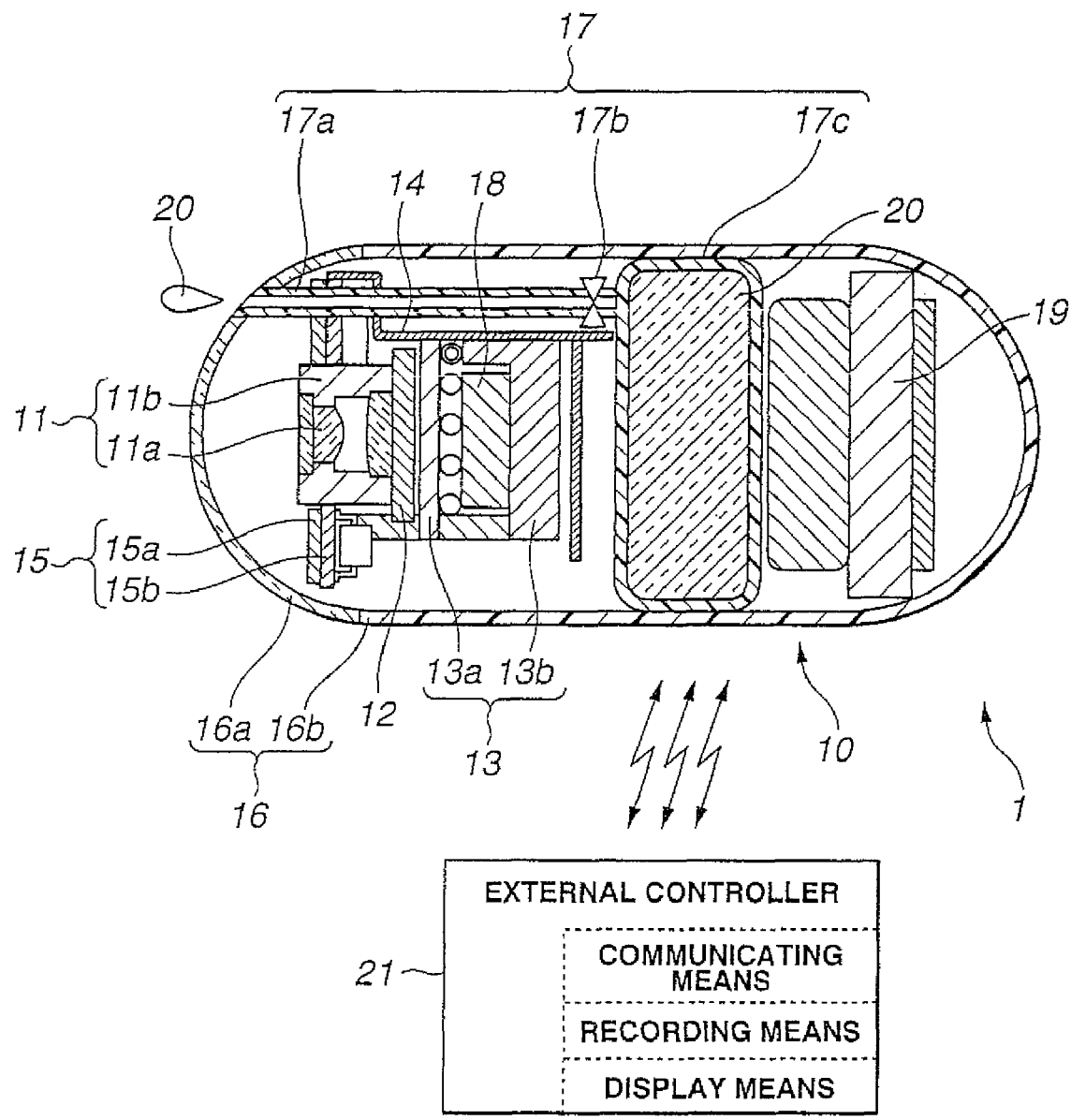
FIG. 1 schematically shows the structure of a capsular endoscope in accordance with a first embodiment of the present invention and the configuration of a capsular endoscope system including the capsular endoscope.

A capsular endoscope in accordance with a first embodiment of the present invention and a capsular endoscope system including the capsular endoscope will be outlined in conjunction with FIG. 1 schematically showing the structure of the capsular endoscope. FIG. 1 shows a section of the capsular endoscope so as to present the internal components.

A capsular endoscope system 1 including the first embodiment comprises, as shown in FIG. 1, a capsular endoscope 10 that has various members incorporated in a capsule-like housing, and an external controller 21 including control means for externally controlling the capsular endoscope 10.

In addition to the control means, the external controller 21 includes: communicating means via which the external controller communicates with the capsular endoscope 10; power feeding means for feeding power, which is required by the internal electric circuits of the capsular endoscope 10, by radio; recording means for receiving and recording an image signal acquired by the capsular endoscope 10; and display means (not shown) on which an image is displayed according to the image signal acquired by the capsular endoscope 10.

Power required by the internal electric circuits of the capsular endoscope 10 is, as mentioned above, fed by radio from the external controller 21. The external controller 21 therefore includes predetermined power feeding means. Accordingly, the capsular endoscope 10 includes a communication/power reception unit 19 that is the mate to the power feeding means.

The capsular endoscope 10 comprises: a housing 16 that is an armor member that seals the interior of the housing in a liquid-tight manner; illuminating means 15 including various members incorporated in the housing 16, light emitting sources 15a formed with light emitting diodes (LED) or the like for illuminating an object such as any of the alimentary organs in a body cavity, and a light emitting source mounting substrate 15b on which the electric circuits for driving or controlling the light emitting sources 15a are mounted; an image pickup optical system 11 including a group of lenses 11a that forms an optical image of the object illuminated by the illuminating means 15 and a lens barrel 11b that holds the group of lenses 11a; image pickup means 12 formed with an image pickup device that receives the optical image of the object formed by the image pickup optical system 11 and that performs predetermined photoelectric conversion so as to produce an image signal; a circuit board 13 including a plurality of substrates 13a and 13b on which an electric circuit for performing various kinds of signal processing (image signal processing and communication) on the image signal received from the image pickup means 12, a control circuit for controlling the internal electric circuits of the capsular endoscope 10 on a centralized basis, and other circuits are mounted; a flexible printed-circuit board (FPC) 14 that electrically links the plurality of substrates included in the circuit board 13 and the substrates and a communication/power reception unit 19 that will be described later; a marker shooting unit 17 (marking means) (which will be detailed later); and posture sensing means 18 mounted on the circuit board 13 for the purpose of sensing the posture of the capsular endoscope 10.

The housing 16 of the capsular endoscope 10 is formed with a rigid member made of, for example, a resin. The housing has: a transparent window 16a which shields and protects the front part of the capsular endoscope 10 and through which illumination luminous flux emanating from the illuminating means 15 or luminous flux incident on the image pickup optical system 11 pass; and a main body 16b that is a main portion of the housing 16 and that encloses and protects various internal members.

The image pickup optical system 11 includes the group of lenses 11a and the lens barrel 11b that holds the group of lenses 11a. The image pickup means 12 is mounted on the mounting surface of the predetermined substrate 13a included in the circuit board 13 located at a predetermined position behind the image pickup optical system 11.

The image pickup means 12 is, as mentioned above, located at the predetermined position behind the image pickup optical system 11. The image pickup means 12 comprises an image pickup device such as a CCD or CMOS that receives an optical image of an object transmitted and formed by the image pickup optical system 11 and performs photoelectric conversion, and an electric circuit that includes a plurality of electric parts and drives the image pickup device to perform predetermined signal processing. The electric circuit and image pickup device are mounted on the predetermined substrate 13a included in the circuit board 13.

Consequently, the illuminating means 15 illuminates an object. Luminous flux reflected from the object is concentrated on the image pickup optical system 11 and transmitted thereby. Thereafter, an optical image of the object is formed on the light receiving surface of the image pickup device included in the image pickup means 12.

The image pickup means 12 performs predetermined signal processing such as photoelectric conversion on the received optical image of the object formed by the image pickup optical system 11, and produces an electric signal (image signal) representing the optical image of the object.

The circuit board 13 comprises, as mentioned above, the plurality of substrates 13a and 13b. For example, electric circuits for performing various kinds of image signal processing, driving and controlling, and signal communication, and a control circuit for controlling the entire capsular endoscope 10 are mounted on the circuit board 13. Each of the electric circuits is realized with, for example, one semiconductor chip.

Now, the detailed structures of the image pickup means 12 and circuit board 13 will be described below.

Figure 2:
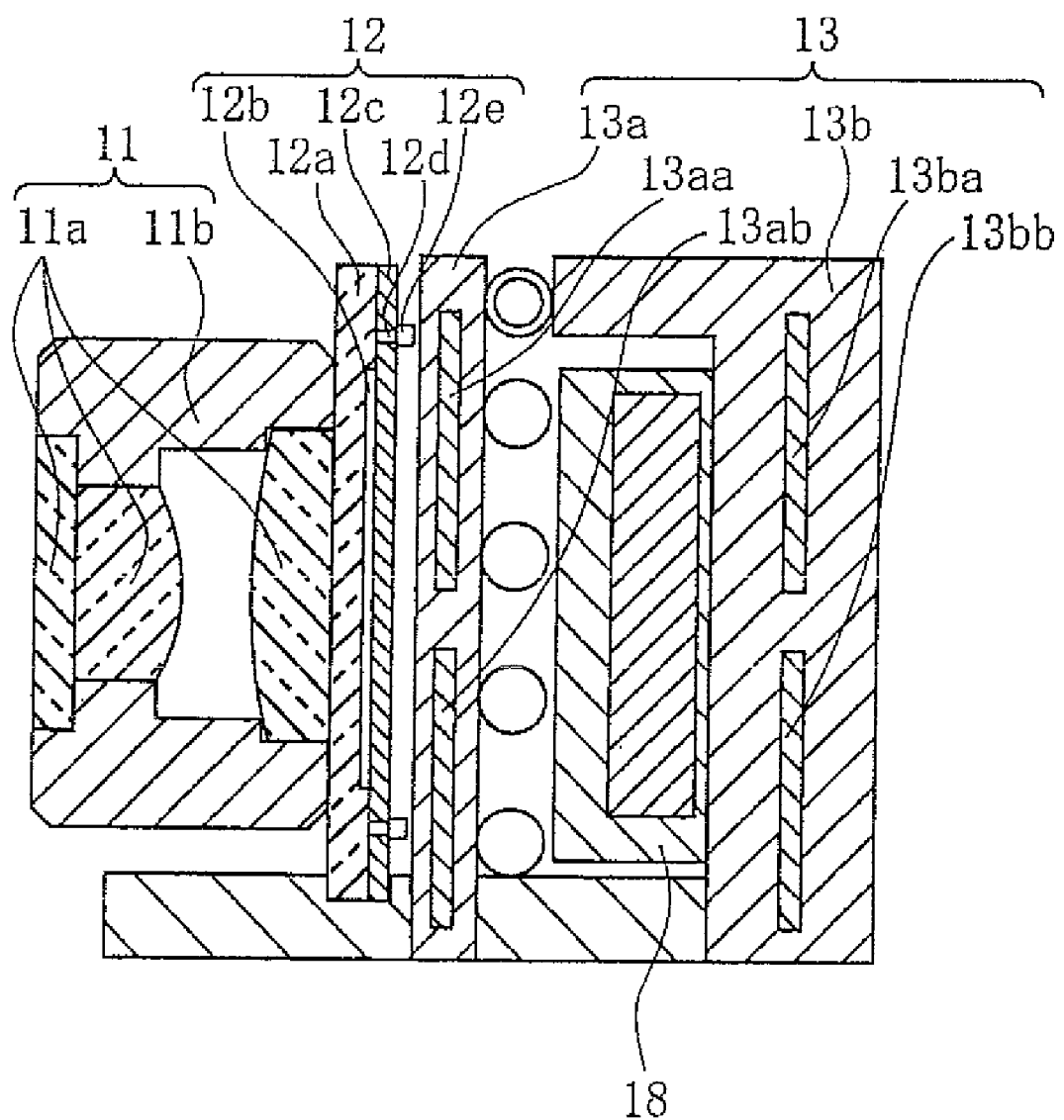
FIG. 2 is an enlarged sectional view showing in enlargement a main portion of the capsular endoscope shown in FIG. 1 including an image pickup optical system, image pickup means, and a circuit board.

FIG. 2 is an enlarged sectional view showing the main portion of the capsular endoscope of the present embodiment including the image pickup optical system, image pickup means, and circuit board. Moreover, FIG. 3A to FIG. 3F schematically show a process of manufacturing the image pickup means. FIG. 3F shows the state of a section of the image pickup means attained at the completion of the process of manufacturing the image pickup means.

The image pickup means 12 is, as shown in FIG. 2 and FIG. 3F, made by joining a glass member 12a and an image pickup device (hereinafter an image sensor) 12c. In this case, the glass member 12a is attached to the front side of the image sensor 12c, that is, the side of the image sensor that faces the image pickup optical system 11 and that forms the image pickup surface.

Electrodes formed on the front side of the image sensor 12c (a junction between the image sensor and glass member 12a) cannot be connected to an external component. In order to connect the electrodes on the front side of the image sensor 12 to a component located behind the rear side of the image sensor 12, the image sensor 12c is provided with penetrating electrodes 12d and projecting electrodes (bumps) 12e. Namely, the electrodes on the front side of the image sensor 12 are connected to a component located behind the rear side thereof via the penetrating electrodes 12d and projecting electrodes 12e.

The penetrating electrodes 12d are realized with very small bores penetrating through the image sensor 12c, and the same number of penetrating electrodes as the number of electrodes is formed. The projecting electrodes 12e are associated with the penetrating electrodes 12d, and are simultaneously formed on a wafer through plating (will be detailed later).

Moreover, the glass member 12a has a concave part formed on the side thereof facing the image sensor 12c. The concave part is intended to hermetically seal the surface of the image sensor 12c when the glass member 12a and image sensor 12c are joined. Consequently, when the glass member 12a and image sensor 12c are joined, an air layer 12b is formed in a predetermined field between them (see FIG. 2 and FIG. 3F).

The image pickup means 12 having the foregoing structure is manufactured according to a process described below.

Figure 3A:
FIG. 3A to FIG. 3F schematically show a process of manufacturing the image pickup means included in the capsular endoscope shown in FIG. 1.
Figure 3B:
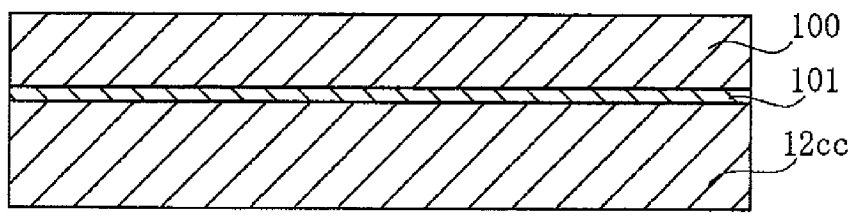

To begin with, a reinforcement member 100 is, as shown in FIG. 3B, temporarily bonded to an image sensor wafer 12cc, which is a raw material as shown in FIG. 3A, using a temporary bonding member 101 such as a predetermined adhesive.

Thereafter, the image sensor wafer 12cc shown in FIG. 3B is polished to have a predetermined thickness using a predetermined machine tool or the like. This results in the state shown in FIG. 3C.

The polishing changes the state of the image sensor wafer 12cc into a state like a very thin film. In this state, it is hard to perform various kinds of machining on the image sensor wafer 12cc.

For this reason, the reinforcement member 100 is bonded to the thin-film image sensor wafer 12cc in order to reinforce the image sensor wafer 12cc for fear the image sensor wafer 12cc may be broken during machining.

Figure 3C:
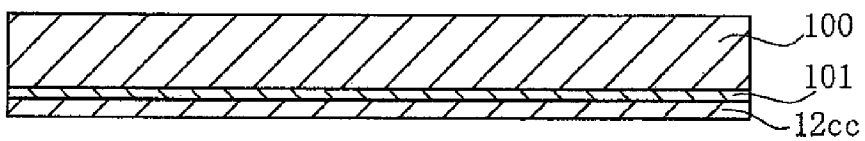

The predetermined number of penetrating electrodes 12d is formed at predetermined positions in the image sensor wafer 12cc (having a specified thickness) in the state shown in FIG. 3C. This brings the image sensor 12c to the state shown in FIG. 3D. For formation of the penetrating electrodes 12d, for example, a dry etching technique is adopted.

Figure 3D:
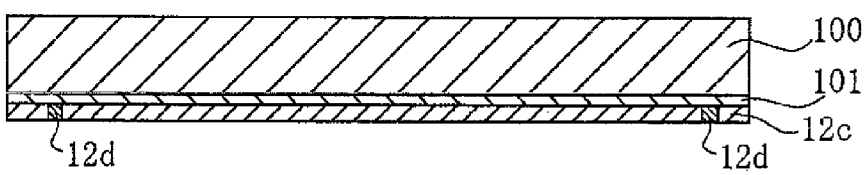

Thereafter, the projecting electrodes 12e are simultaneously formed over the penetrating electrodes 12d in the image sensor 12c shown in FIG. 3D by performing plating or the like. This brings the image sensor 12c to the state shown in FIG. 3E.

Figure 3E:
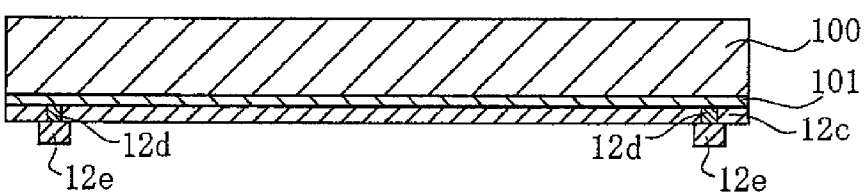
Figure 3F:
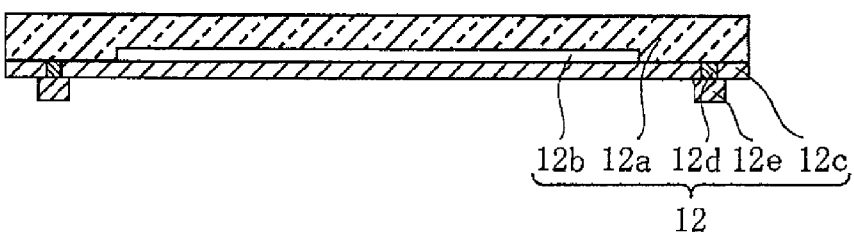

The reinforcement member 100 and temporary bonding member 101 are removed from the image sensor in the state shown in FIG. 3E. Thereafter, the glass member 12a is bonded to the predetermined side (front side) of the image sensor 12c. This results in the state shown in FIG. 3F. The side of the glass member 12a having the concave part is opposed to the front side (image pickup surface) of the image sensor 12c. Consequently, the air layer 12b is formed in the predetermined field between the glass member 12a and image sensor 12c. This is the state attained when the manufacture of the image pickup means 12 is completed, that is, the state shown in FIG. 3F. The image pickup means 12 is mounted on the substrate 13a included in the circuit board 13.

The substrates 13a and 13b constituting the circuit board 13 have, as shown in FIG. 2, for example, an inductor 13aa, an integrated circuit (IC) 13ab, a thin film resistor 13ba, and a capacitor 13bb embedded therein.

Referring back to FIG. 1, the posture sensing means 18 is mounted on the substrate 13b that is included in the circuit board 13 and that is located substantially in the center of the capsular endoscope 10. The posture sensing means 18 is realized with a gyroscope or the like for sensing the three-dimensional posture of the capsular endoscope 10 that is inserted into a body cavity and put to use. Based on data detected by the posture sensing means 18, the posture of the capsular endoscope 10 is controlled.

Moreover, the communication/power reception unit 19 is, as mentioned above, disposed at a predetermined position near one end of the capsular endoscope 10 within the capsular endoscope 10. The communication/power reception unit 19 fills the role of means via which the capsular endoscope 10 communicates with the external controller 21, and also fills the role of means for receiving power from the external controller 21.

Specifically, the communication/power reception unit 19 comprises: radio-communication means realized with an antenna member or the like via which various communication signals are transferred between the capsular endoscope 10 being used in, for example, a body cavity and the external controller 21 located outside the body cavity or via which an image signal representing an object and being acquired by the capsular endoscope 10 is transmitted to the external controller 21; and power receiving means for receiving power fed by radio from the external controller 21 and distributing the power to the internal electric circuits of the capsular endoscope 10.

The communication/power reception unit 19 comprises, for example, an electric double-layer capacitor (so-called super capacitor), a non-directional antenna, a voltage-controlled oscillator (communicating means), a regulator, and a power receiving antenna (power receiving means).

The illuminating means 15 comprises the light emitting sources 15a realized with a plurality of light emitting diodes (LEDs) for illuminating an object, and the light emitting source mounting substrate 15b on which the light emitting sources 15a are mounted and on which an electric circuit for driving or controlling the light emitting sources 15a is also mounted.

To be more specific, the plurality of light emitting sources 15a is located near the periphery of the lens barrel 11b of the image pickup optical system 11. The plurality of light emitting diodes realizing the respective light emitting sources 15a is disposed so that predetermined luminous flux will be emitted to the front side of the capsular endoscope 10.

Moreover, the marker shooting unit 17 serving as marking means that shoots a predetermined marker member 20 (which will be detailed) so as to indwell it in a body cavity is located at a predetermined position in the capsular endoscope 10. The marker shooting unit 17 comprises a nozzle 17a, a reservoir 17c, and the marker member 20 poured into the reservoir 17c.

The reservoir 17c is located behind the light emitting source mounting substrate 15b within the housing 16 of the capsular endoscope 10, or in other words, is located substantially in the center of the capsular endoscope 10. The reservoir 17c is filled with the marker member 20 that is pressurized in advance. The marker member 20 is shot to adhere to any region in a body cavity for the purpose of marking a lesion or the like.

As the marker member 20, for example, a fluorescent substance, a substance opaque to X-rays, or a dye that is a liquid is adopted. Means for pressurizing the marker member 20 pressurizes the marker member 20 in advance by utilizing, for example, an electromagnetic force or an electrostatic force.

The nozzle 17a is realized with a tubular member whose diameter is very small. The nozzle 17a extends from a predetermined portion of the reservoir 17c through the light emitting source mounting substrate 15b to the transparent window 16a of the housing 16. The distal part of the nozzle 17a lies at a predetermined position near the transparent window 16a so that it will not jut out of the external surface of the transparent window 16a. Moreover, the distal part of the nozzle 17a is disposed to fall within the field of view offered by the image pickup optical system 11.

A valve 17b is disposed in a predetermined portion of the nozzle 17a (near the reservoir 17c). The valve 17b is realized with a piezoelectric valve that opens or closes due to the piezoelectric effect, a pneumatic valve that opens or closes with air pressure, or an electromagnetic valve that utilizes electromagnetism. Consequently, the reservoir 17c and nozzle 17a freely communicate with each other by opening the valve 17b.

When the valve 17b is opened, the marker member 20 in the reservoir 17c is shot to a target object such as a target lesion, which is located externally ahead of the capsular endoscope 10, over the nozzle 17a due to the internal pressure of the reservoir 17c.

Controlling shooting of the marker member 20 to be achieved by opening or closing the valve 17b is executed remotely using the external controller 21. Namely, an operator of the system 1 manipulates a predetermined manipulation member of the external controller 21, whereby the shooting is controlled. The marker shooting unit 17 serves as shooting means for shooting the marker member 20.

On the other hand, the external controller 21 comprises: as mentioned previously, the control means that is used mainly to externally control the capsular endoscope 10 and that controls the entire system on a centralized manner; image processing means for receiving an image signal or the like that is acquired by the capsular endoscope 10 and transmitted by radio from the radio-communication means included in the capsular endoscope 10, and performing predetermined signal processing; communicating means via which the external controller 21 communicates with the capsular endoscope 10; recording means for recording the received image signal; display means on which a discernible image is displayed according to the image signal having undergone the predetermined signal processing; and power feeding means for feeding required power to the capsular endoscope 10 by radio.

As the display means, for example, a cathode-ray tube (CRT) type display device, a liquid crystal display device, a plasma display device, an electroluminescent display device, or any other typical display device is adopted.

The operation of the capsular endoscope 10 having the foregoing components and the operation of the capsular endoscope system 1 including the capsular endoscope 10 will be described below.

To begin with, the capsular endoscope 10 inserted into a body cavity acquires an image signal representing a desired object, performs predetermined processing on the image signal, and transmits the resultant signal to the external controller 21 via the communication/power reception unit 19. The concrete process will be described below.

In order to perform examination using the capsular endoscope 10, first, a subject is asked to gulp down the capsular endoscope 10.

The capsular endoscope 10 advances along a body cavity due to the peristalsis of each of the subject's intracavitary organs or predetermined moving means, and duly reaches a target region (near an object) whose observation and examination is desired. At this time, the external controller 21 starts feeding power to the capsular endoscope 10.

The timing of feeding power from the external controller 21 to the capsular endoscope 10 is not limited to the above one. Alternatively, the feeding of power may be started immediately before a subject gulps down the capsular endoscope 10 or may be started according to any other timing.

When the capsular endoscope 10 is activated with the power received from the external controller 21, the illuminating means 15 is turned on at the same time. The capsular endoscope 10 moves while the illuminating means 15 is illuminating the interior of the body cavity. At this time, the image pickup optical system 11 forms an intracavitary optical image on the light receiving surface of the image pickup means 12.

The image pickup means 12 in turn performs predetermined photoelectric conversion. An electric signal (image signal) representing an image equivalent to the optical image of the object is produced through the photoelectric conversion. The image signal is transmitted to a predetermined device mounted on the circuit board 13 over the flexible printed-circuit board 14, and then subjected to various kinds of signal processing.

The resultant image signal representing the object image is transmitted to the external controller 21 via the communication/power reception unit 19. The external controller 21 in turn performs predetermined processing on the received image signal. Thereafter, an electric signal of a predetermined form that can be handled by the recording means or display means included in the external controller, that is, a recording image signal suitable for recording or a display image signal suitable for display is transmitted to the recording means or display means.

Specifically, the image signal of the object is converted into the recording image signal of a predetermined form suitable for recording, transferred to the recording means, and then recorded in a predetermined recording field on a predetermined recording medium (not shown but included in the recording means). Moreover, the image signal is also converted into the display image signal of a predetermined form suitable for display, transferred to a display device, and displayed as a discernible image using a display unit of the display device.

Consequently, the image of the object displayed on the display unit of the display device is viewed in order to examine and diagnose the object.

When the capsular endoscope 10 inserted into the body cavity as mentioned above stays near the region (object) desired to be observed and examined, the operator of the system 1 manipulates the external controller 21 so as to actuate the marker shooting unit 17 incorporated in the capsular endoscope 10, and thus controls shooting of the marker member 20.

At this time, since the nozzle 17a of the marker shooting unit 17 falls within the field of view offered by the image pickup optical system 11, at least the distal part of the nozzle 17a is visualized together with the object by means of the display unit (not shown) of the display device included in the external controller 21. Therefore, the operator manipulates the marker shooting unit 17 so as to shoot the marker member 20 while viewing the image of the object that is a target to be marked with the marker member 20, and the image of the nozzle 17a alike.

Consequently, a predetermined amount of the marker member 20 is shot from the marker shooting unit 17. The marker member 20 is indwelled in the desired target region in the body cavity. Thus, the object such as a lesion is marked.

The shooting should be performed at least once during one examination. Alternatively, the shooting may be performed a plurality of times.

As described above, the first embodiment includes the marker shooting unit 17 serving as marking means. While the image pickup means 12 is used to observe the inside of a body cavity, the marker member 20 is indwelled in an object that is a desired region, for example, a lesion in order to mark the object. Therefore, after the capsular endoscope 10 is used for examination, when another examination is performed, the object such as a previously discovered lesion can be rediscovered readily.

In this case, assuming that a dye is adopted as the marker member 20, when examination is performed later, for example, when close examination is performed using an ordinary endoscope or the like, the region (object such as a lesion) in which the marker member 20 is indwelled can be rediscovered readily.

Moreover, assuming that a fluorescent substance is adopted as the marker member 20, the lesion or the like can be readily rediscovered by performing fluorescent observation.

Assuming that a substance opaque to X-rays is adopted as the marker member 20, after examination is performed using the capsular endoscope 10, radiographic examination is carried out in order to extracorporeally accurately grasp the position of a region such as a lesion.

Moreover, since the nozzle 17a of the marker shooting unit 17 falls within the field of view offered by the image pickup optical system 11, the distal part of the nozzle 17a and an object can be simultaneously visualized using the display unit (not shown) of the display device included in the external controller 21. Consequently, shooting is performed readily using the marker shooting unit 17.

According to the first embodiment, the reservoir 17c is, as shown in FIG. 1, fixed at a predetermined position in the capsular endoscope 10. If this structure is adopted, the same number of types of capsular endoscopes 10 as the number of kinds of marker materials 20 to be poured into the reservoir 17c must be made available. A desired capsular endoscope 10 would be selected from among the plurality of types of capsular endoscopes 10 according to the examination to be performed.

Otherwise, for example, the reservoir 17c may be formed as a unit so that it can be freely attached or detached to or from the capsular endoscope 10.

In this case, when the use of the capsular endoscope 10 is started, a reservoir unit filled with a desired marker member 20 suitable for an intended examination is selected, and attached to the capsular endoscope 10.

Namely, in this case, the main body structure of the capsular endoscope 10 is used in common, and the reservoir unit alone is selected arbitrarily and attached to the main body of the capsular endoscope 10. Thus, the marker member 20 suitable for the desired examination can be selected accordingly.

Consequently, a system enabling efficient management of resources can be configured. Moreover, talking of manufacture, only reservoir units should be manufactured and managed in association with the kinds of marker member 20. This leads to an efficient manufacturing process and contributes to reduction of the cost of manufacture.

According to the first embodiment, as a method of feeding power to the capsular endoscope 10, an externally power feeding method using the communication/power reception unit 19 that receives power fed from the external controller 21 by radio is adopted. Alternatively, any other different power feeding method, for example, a built-in power supply method in which a source battery composed of primary or secondary cells is incorporated in the capsular endoscope 10 may be adopted for the capsular endoscope 10.

In this case, the power feeding means need not be included in the external controller 21. A communication unit equivalent to the communication/power reception unit 19 that has power receiving means removed therefrom is adapted to the capsular endoscope 10.

Although the usable time during which the capsular endoscope is usable depends on the battery capacity, the internal electric circuitry of the capsular endoscope can be simplified. This contributes to reduction of the cost of manufacture.

According to the first embodiment, the marker member 20 with which an object and its surroundings are marked is poured into the reservoir 17c included in the marker shooting unit 17. Instead of the marker member 20, an agent for medical or therapeutic treatment that acts on a lesion or the like may be poured into the reservoir 17c.

In this case, the capsular endoscope 10 is used to acquire an optical image and a reconstructed image is displayed, whereby visual examination is carried out. Moreover, if a lesion is discovered during the examination, the marker shooting unit 17 is used to shoot the agent. Thus, simple therapeutic or medical treatment can be achieved.

On the other hand, according to the first embodiment, a liquid member is shot as the marker member 20 to an object. The marker member 20 is not limited to the liquid member. Alternatively, the marker member 20 may be, for example, like the one employed in a second embodiment of the present invention shown in FIG. 4 and FIG. 5.

Figure 4:
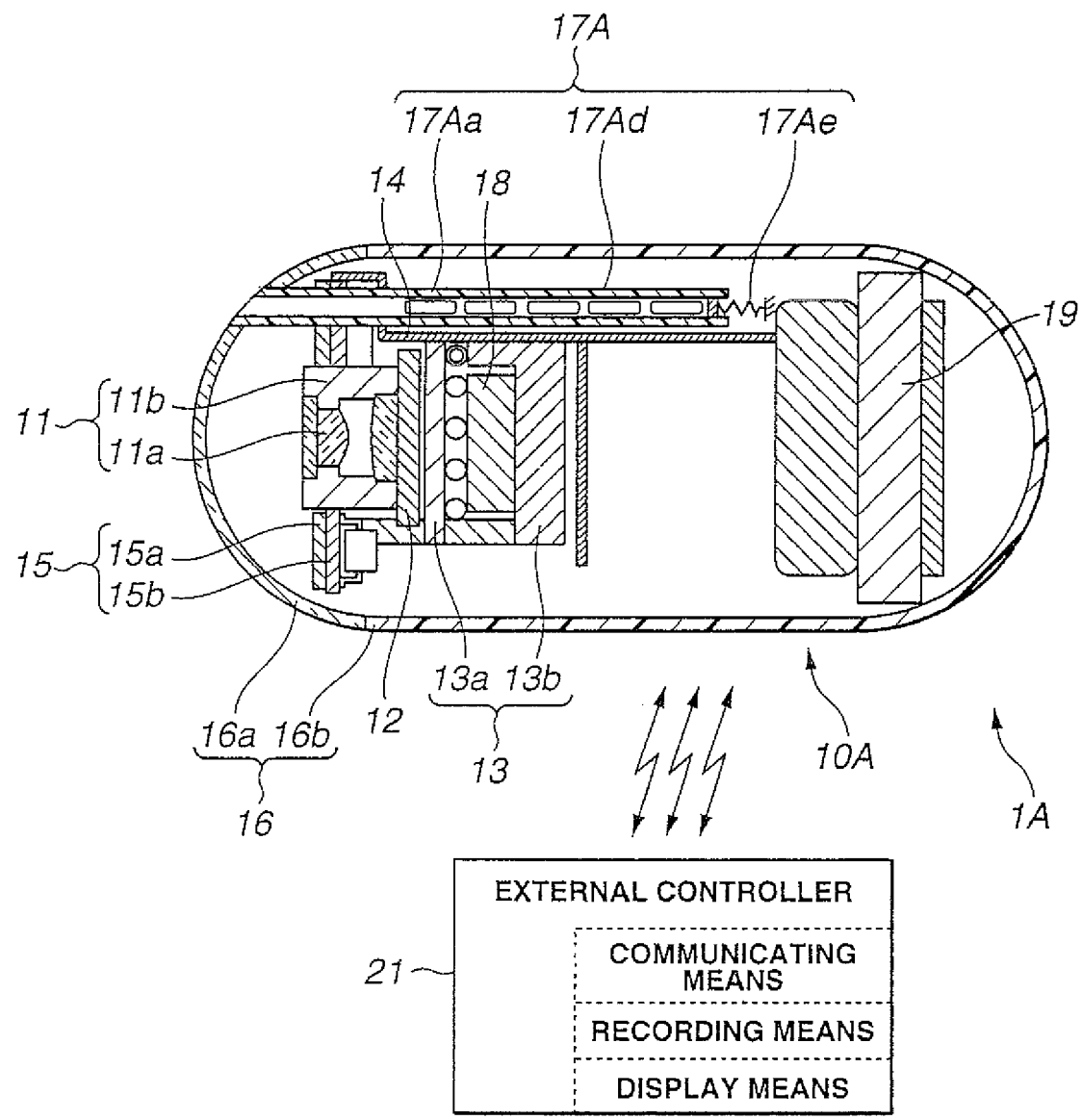
FIG. 4 schematically shows the structure of a capsular endoscope in accordance with a second embodiment of the present invention and the configuration of a capsular endoscope system including the capsular endoscope.
Figure 5:
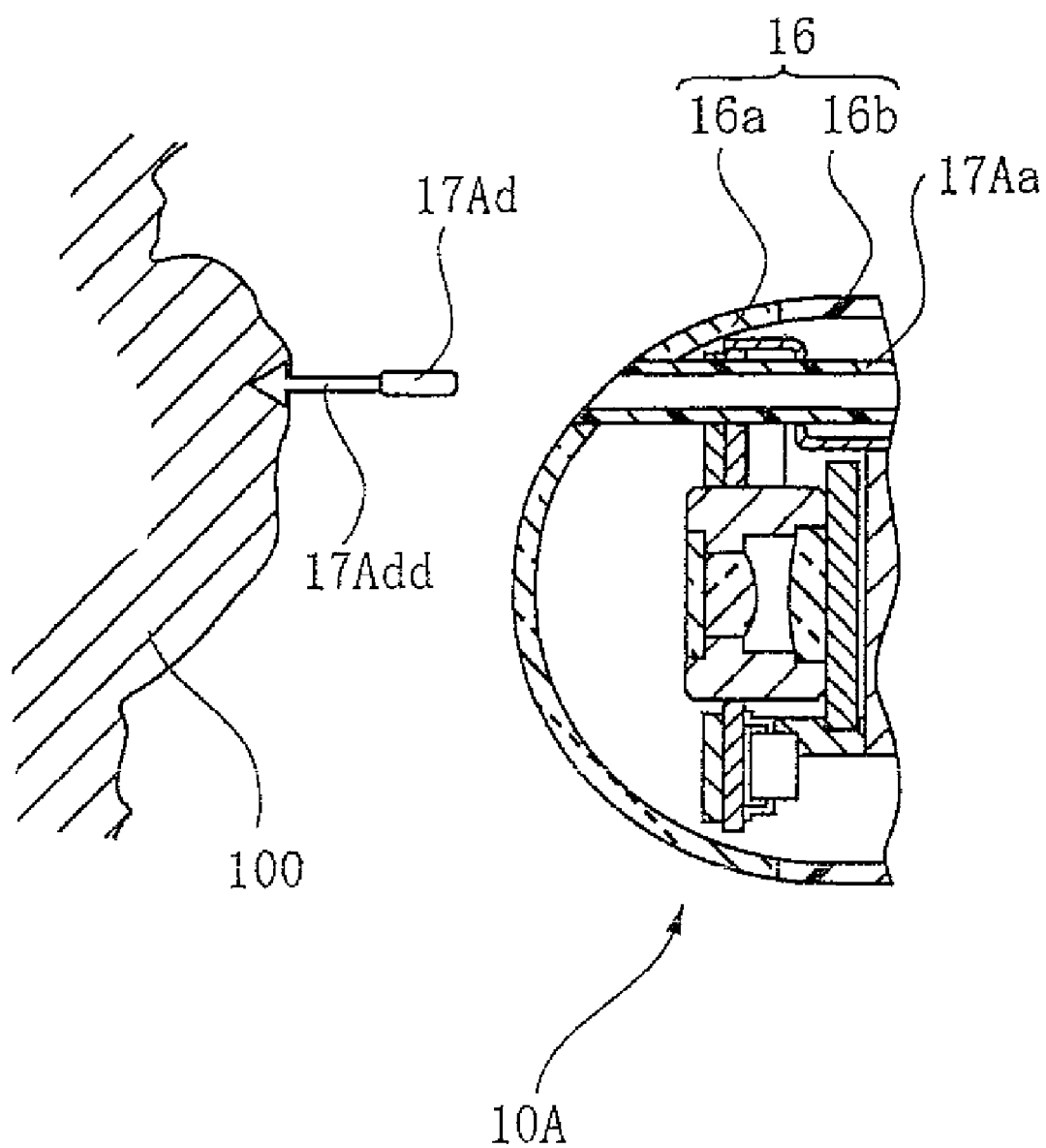
FIG. 5 is an enlarged sectional view showing a main portion of the capsular endoscope shown in FIG. 4 including the distal part thereof.

FIG. 4 schematically shows the structure of a capsular endoscope in accordance with the second embodiment of the present invention and the configuration of a capsular endoscope system including the capsular endoscope. FIG. 4 shows a section of the capsular endoscope to present the internal components thereof. FIG. 5 is an enlarged sectional view showing a main portion of the capsular endoscope 10 including the distal part thereof, wherein a solid marker member is shot from the capsular endoscope in order to mark a desired object.

The present embodiment has, as shown in FIG. 4, substantially the same components as the aforesaid first embodiment does. A marker shooting unit incorporated in the capsular endoscope is a bit different from the one included in the first embodiment. Therefore, the same reference numerals will be assigned to the components of the present embodiment identical to those of the first embodiment, and the description of the identical components will be omitted. Different components alone will be described in conjunction with FIG. 4 and FIG. 5 below.

A marker shooting unit 17A included in the present embodiment is designed to shoot a marker member 17Ad formed with a clip-like solid. The marker shooting unit 17A comprises a cylindrical shooting pipe 17Aa and a constraining member 17Ae such as a spring for shooting the marker material 17Ad.

A plurality of marker members 17Ad is incorporated in the shooting pipe 17Aa. A predetermined mechanism is constructed so that the constraining member 17Ae can shoot the marker members 17Ad to outside at any time.

The marker members 17Ad are members formed with, as mentioned above, clip-like solids, for example, metallic members. When the marker members 17Ad are incorporated in the shooting pipe 17Aa, they have a substantially particulate shape as shown in FIG. 4. When the marker members 17Ad are shot at any time, a needle-like portion 17Add is, as shown in FIG. 5, jutted substantially out of the distal end of each of the marker members. The needle-like portion 17Add pieces an object 103 and is thus indwelled in the region.

The other components are identical to those of the first embodiment. The operation of the present invention is substantially identical to that of the first embodiment except the working of the marker members 17Ad to be shot from the marker shooting unit 17A.

As mentioned above, according to the second embodiment, the same advantages as those of the first embodiment can be provided.

Moreover, according to the present embodiment, the solid marker members 17Ad formed with metallic members or the like are indwelled in a desired intracavitary region. After examination is performed using the capsular endoscope 10A, if radiographic examination is carried out, the position of a lesion or the like can be accurately extracorporeally grasped.

Next, a capsular endoscope in accordance with a third embodiment of the present invention and a capsular endoscope system will be described below.

Figure 6:
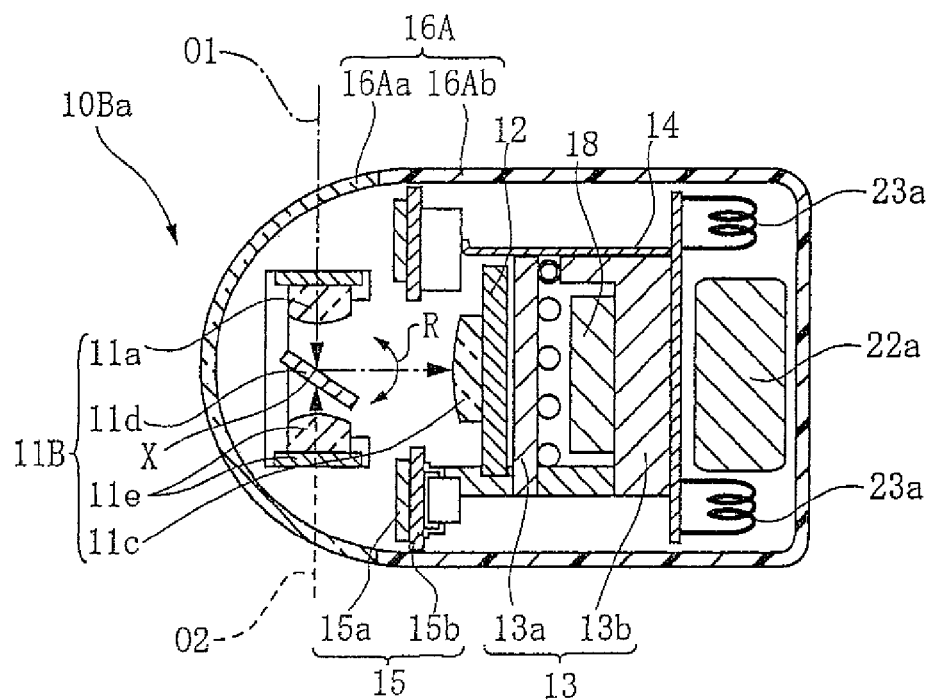
FIG. 6 schematically shows the structure of a main capsule that is one portion of a capsular endoscope in accordance with a third embodiment of the present invention.
Figure 7:
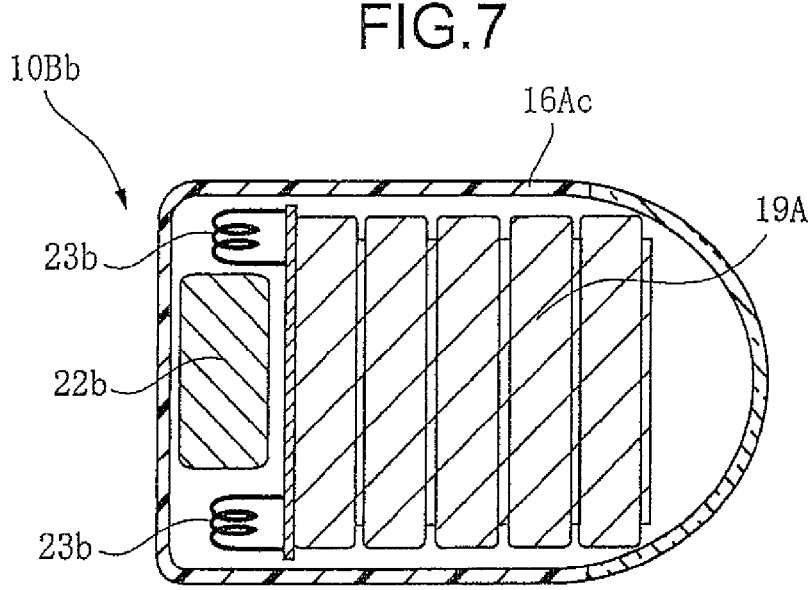
FIG. 7 schematically shows the structure of a power capsule that is the other portion of the capsular endoscope in accordance with the third embodiment of the present invention.
Figure 8:
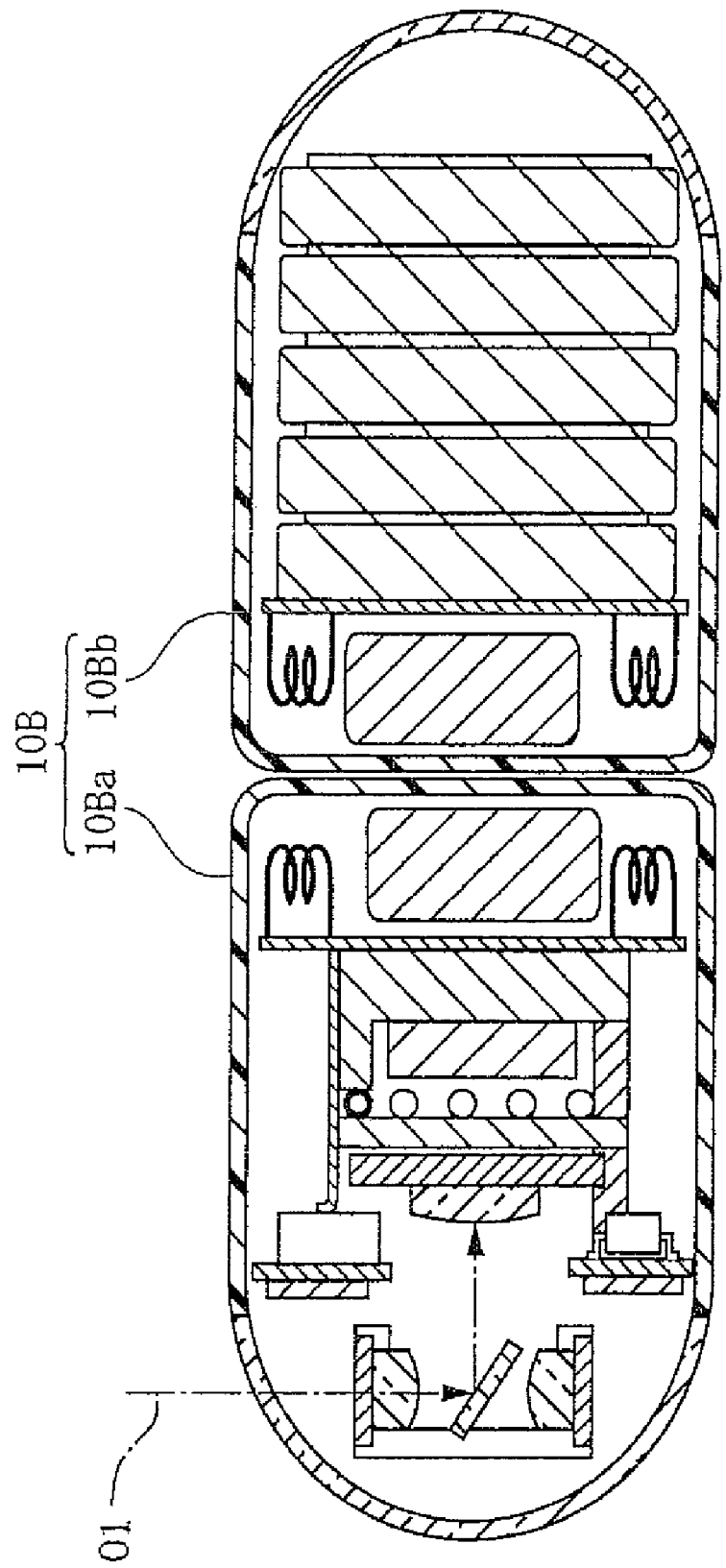
FIG. 8 schematically shows the use state of the capsular endoscope in accordance with the third embodiment of the present invention.

FIG. 6 to FIG. 8 show the capsular endoscope in accordance with the present embodiment. FIG. 6 schematically shows a main capsule that is part of the capsular endoscope. FIG. 7 schematically shows a power capsule that is other part of the capsular endoscope. FIG. 8 shows the use state of the capsular endoscope in which the main capsule shown in FIG. 6 and the power capsule shown in FIG. 7 are coupled to each other.

A capsular endoscope 10B in accordance with the present embodiment comprises two capsular housings, that is, as shown in FIG. 6, a main capsule 10Ba accommodating major members that include image pickup means, and a power capsule 10Bb accommodating members that constitute power supply means and include a source battery as shown in FIG. 7. The two separate capsules (main capsule 10Ba and power capsule 10Bb) are coupled to each other using predetermined coupling means (that will be detailed later). When the two capsules are coupled to each other, they function as the capsular endoscope 10B.

The same reference numerals will be assigned to the internal components of the capsular endoscope 10B in accordance with the present invention which have the same capabilities as those of the capsular endoscope 10 in accordance with the first embodiment. The description of the identical components will be omitted. FIG. 8 shows, as mentioned above, the main capsule shown in FIG. 6 and the power capsule shown in FIG. 7 that are coupled to each other. The reference numerals are omitted from FIG. 8 in efforts to avoid the complexity of the drawing.

The main capsule 10Ba comprises a housing 16A serving as an armor member that seals the interior thereof in a liquid-tight manner and various members incorporated in the housing 16A.

The housing 16A is shaped like a capsule whose one end is made planar. Specifically, the housing 16A is shaped like a hollow hemisphere using a rigid member made of, for example, a transparent resin. The housing 16A comprises: a transparent window 16Aa that covers and protects the front side of the capsular endoscope 10B and that transmits illumination luminous flux emitted from the illuminating means 15 and luminous flux incident on an image pickup optical system 11B; and a main body 16Ab that is shaped substantially like a cylinder, of which one end has an opening, using a rigid member made of, for example, a resin, that serves as a main portion of the housing 16A, and that externally covers and protects various members incorporated therein.

In the housing 16A, as shown in FIG. 6, the image pickup optical system 11B, the image pickup means 12, a circuit board 13 including a plurality of substrates 13a and 13b, a flexible printed-circuit board 14, the illuminating means 15 including light emitting sources 15a and a light emitting source mounting substrate 15b, the posture sensing means 18, a permanent magnet 22a serving as coupling means, and a transformer 23a are disposed at predetermined positions.

The image pickup optical system 11B selectively introduces one of luminous fluxes (O1 and O2 in FIG. 6), which fall thereon in two predetermined lateral directions relative to the longitudinal-axis direction of the capsular endoscope 10B, into the light receiving surface of the image pickup means 12.

The image pickup optical system 11B therefore comprises a first group of lenses 11a and a second group of lenses 11e that are opposed to each other in order to introduce luminous fluxes which fall thereon in two different directions, a third group of lenses 11c located near the front side of the light receiving surface of the image pickup means 12, and a reflecting mirror 11d that receives one of the luminous fluxes transmitted by the first group of lenses 11a and the second group of lenses 11e and introduces the luminous flux to the third group of lenses 11c.

The reflecting mirror 11c is disposed to freely swivel in the directions of arrows R within a predetermined range centered on a position X shown in FIG. 6. In this case, the movable range of the reflecting mirror 11c is a range defined between a position at which the reflecting mirror meets the ray axis O1 of the luminous flux transmitted by the first group of lenses 11a at an angle of substantially 45° and a position at which the reflecting mirror meets the ray axis O2 (indicated with a dashed line) of the luminous flux transmitted by the second group of lenses 11e at an angle of substantially 45°.

In the present embodiment, communicating means via which the capsular endoscope 10B communicates with an external controller (not shown) is mounted on the circuit board 13.

On the other hand, the power capsule 10Bb comprises a housing 16Ac serving as an armor member that seals the interior thereof in a liquid-tight manner and various members incorporated in the housing 16Ac.

The housing 16Ac is shaped substantially like the housing 16R of the main capsule 10Ba as a whole. The entire housing 16Ac is formed with a rigid member made of a resin in the same manner as the main body 16Ab of the main capsule 102Ba is.

The housing 16Ac accommodates a source battery 19A including a plurality of primary or secondary cells, a permanent magnet 22b serving as coupling means, and transformers 23b.

The permanent magnet 22b exhibits a polarity opposite to the polarity of the permanent magnet 22a included in the main capsule 10Ba. Consequently, the main capsule 10Ba and power capsule 10Bb (housing 16Ab and housing 16Ac) are coupled to each other as shown in FIG. 8 owing to magnetic forces induced by the permanent magnet 22a included in the main capsule 10Ba and the permanent magnet 22b included in the power capsule 10Bb.

Moreover, when the transformers 23b are used in combination with the transformers 23a included in the main capsule 10Ba, power can be fed in a non-contact state.

Specifically, when the main capsule 10Ba and power capsule 10Bb are coupled to each other as shown in FIG. 8, if the transformers are actuated, although the transformers do not come into contact with each other, power is fed from the power capsule 10Bb to the main capsule 10Ba.

The operation of the capsular endoscope 10B in accordance with the present embodiment having the foregoing components will be described below.

When the capsular endoscope 10B is used for examination, a subject is first asked to gulp down the main capsule 10Ba and the power capsule 10Bb separately. The main capsule and power capsule are coupled to each other in a body cavity owing to the attractions of the permanent magnets 22a and 22b.

When the main capsule and power capsule are coupled to each other as shown in FIG. 8, the transformers 23a and 23b are actuated. Predetermined power is fed from the power capsule 10Bb to the main capsule 10Ba, whereby the capsular endoscope 10B starts functioning.

The orientation of the reflecting mirror 11d included in the image pickup optical system 11B is controlled by the external controller (not shown). Consequently, an object located in one of two predetermined lateral directions of the capsular endoscope 10B can be selectively observed. In the state shown in FIG. 8, the reflecting mirror 11d is positioned in order to introduce luminous flux, which is transmitted by the first group of lenses 11a, to the image pickup means 12.

After examination is completed, the capsular endoscope 10B is evacuated due to the peristalsis of each of the subject's intracavitary organs.

As described above, according to the third embodiment, the main capsule 10Ba and power capsule 10Bb are formed separately from each other, and coupled using the permanent magnets 22a and 22b. When the main capsule and power capsule are coupled to each other, power is fed from the power capsule 10Bb to the main capsule 10Ba.

Consequently, the unit size of each of the capsules can be reduced.

Moreover, even if the sizes of the capsules are increased, a subject can gulp down the capsules. The size of a capsular endoscope can be increased without an increase in a load on the subject. This means that each of the capsules can offer a large volume. Owing to the larger volume, for example, the main capsule 10Ba can accommodate a larger number of members. Eventually, higher performance and a larger number of capabilities can be realized. Moreover, for example, the power capsule 10Bb can accommodate a larger number of source cells. This contributes to extension of a use time. Furthermore, a different kind of source battery, for example, a generation device composed of, for example, fuel cells but not of primary or secondary cells can be incorporated in the power capsule.

According to the third embodiment, the permanent magnets 22a and 22b are adopted as the coupling means for coupling the main capsule 10Ba and power capsule 10Bb. The coupling means is not limited to the permanent magnets.

For example, at least one of the permanent magnets 22a and 22b may be replaced with an electromagnet. In this case, when the external controller is used to control the magnetic force of the electromagnet, the main capsule 10Ba and power capsule 10Bb can be uncoupled from each other at any time. After the main capsule and power capsule are gulped down separately from each other, they are coupled to each other in order to perform desired examination. Thereafter, the main capsule and power capsule are uncoupled from each other. In this case, the capsules 10Ba and 10Bb can be evacuated readily.

According to the third embodiment, the source battery is incorporated in the power capsule 10Bb. Aside from the source battery, power receiving means for receiving power externally fed by radio may be included as it is included in the first embodiment. In this case, both the source battery and power receiving means are used to adopt both the built-in power method and externally power feeding method. Otherwise, one of the methods may be adopted.

According to the third embodiment, the image pickup optical system 11B is designed so that an object located in one of two predetermined lateral directions of the capsular endoscope 10B can be selectively observed. Alternatively, the image pickup optical system may be designed so that a predetermined range defined in one of the lateral directions of the capsular endoscope 10B or defined ahead of the capsular endoscope 10B can be observed.

Figure 9:
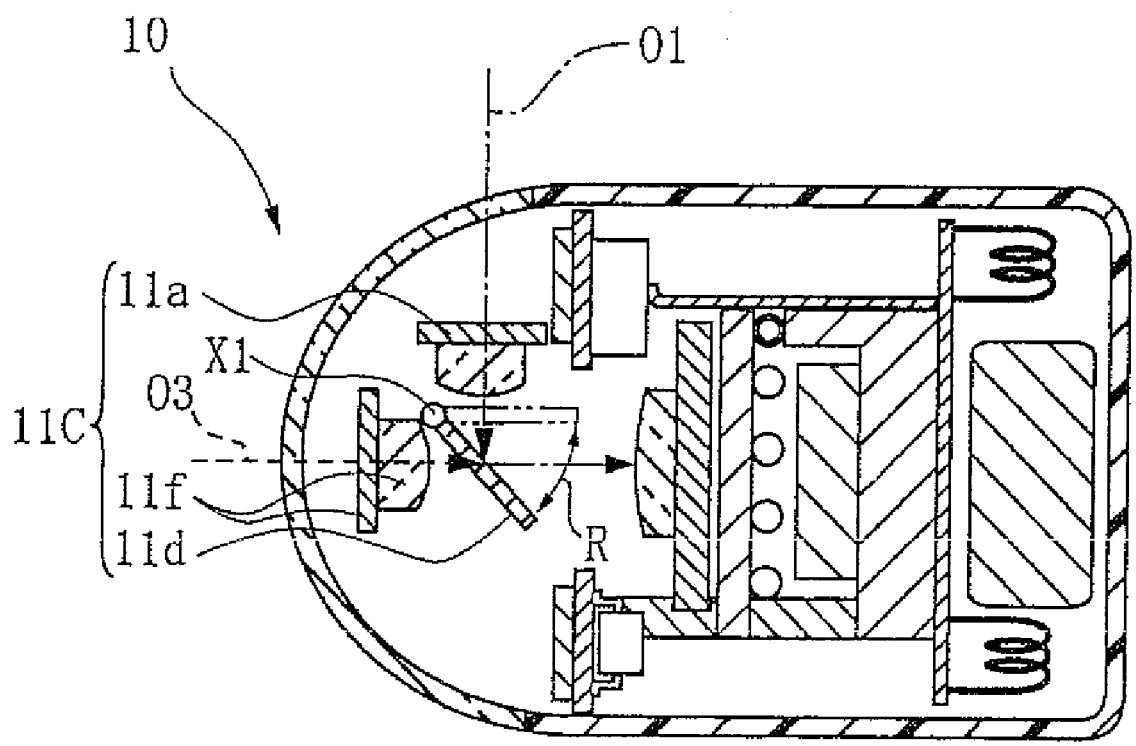
FIG. 9 schematically shows a main capsule included in a capsular endoscope in accordance with a variant of the third embodiment of the present invention.

FIG. 9 schematically shows the structure of a main capsule included in a capsular endoscope in accordance with a variant of the third embodiment of the present invention.

The variant, as shown in FIG. 9, is different from the third embodiment in the optical elements of an image pickup optical system 11C that is one of the components of a main capsule 10Ca. Therefore, the components of the main capsule 10Ca other than the image pickup optical system 11C and the components of the power capsule are identical to those of the third embodiment. The illustration and description of the identical components will therefore be omitted.

The image pickup optical system 11C incorporated in the main capsule 10Ca included in the capsular endoscope in accordance with the variant comprises two groups of lenses that introduce luminous fluxes which fall thereon in two different directions, that is, a first group of lenses 11a and a second group of lenses 11f, a third group of lenses 11c disposed near the front side of the light receiving surface of the image pickup means 12, and a reflecting mirror 11d that receives one of the luminous fluxes transmitted by the first group of lenses 11a and second group of lenses 11f and introduces the luminous flux to the third group of lenses 11c as shown in FIG. 9.

The first group of lenses 11a out of the two groups of lenses is, similarly to the one included in the third embodiment, located at a position at which the first group of lenses can transmit luminous flux falling thereon in a predetermined one of the lateral directions of the capsular endoscope, whereby a lateral field of view is ensured. Moreover, the second group of lenses 11f is located at a position at which the second group of lenses can transmit luminous flux falling thereon from ahead of the capsular endoscope, whereby a front field of view is ensured.

The reflecting mirror 11c is disposed so that it can freely swivel in the directions of arrows R within a predetermined range centered on a position X1 in FIG. 9. In this case, the movable range of the reflecting mirror 11c is defined between a position (indicated with a solid line in FIG. 9) at which the reflecting mirror 11c meets the ray axis O1 of luminous flux, which has passed through the first group of lenses 11a, at an angle of substantially 45° and a position (indicated with an alternate long and two short dashes line in FIG. 9) at which the reflecting mirror recedes from luminous flux (ray axis O3) that has passed through the second group of lenses 11f. The other components and operations thereof are substantially identical to those of the third embodiment.

As described above, even the variant provides the same advantages as the third embodiment does. In addition, either of the front field of view and the lateral field of view offered by the capsular endoscope can be selected for observation.

According to the present invention, it is apparent that a wide range of different embodiments can be constructed based on the invention without a departure from the spirit and scope of the invention. The present invention will be limited to the appended Claims but not restricted to any specific embodiment.

What is claimed is:

1. A capsular endoscope comprising:
a first capsular housing containing a power supply;
a second capsular housing containing an image pickup optical system, an illumination unit and a circuit board;
coupling means for coupling the first capsular housing and the second capsular housing in a body cavity, the first capsular housing and the second capsular housing being swallowed separately by a subject, and the coupling means being disposed inside the first capsular housing and the second capsular housing; and
power feeding means for feeding power from the power supply only when the first capsular housing and the second capsular housing are coupled, the power feeding means being disposed in the first capsular housing and the second capsular housing.

2. The capsular endoscope according to claim 1, wherein the coupling means is a permanent magnet.

3. The capsular endoscope according to claim 1, wherein the coupling means is an electromagnet.

4. The capsular endoscope according to claim 1, wherein the power feeding means includes a transformer.

5. The capsular endoscope according to claim 1, wherein the power supply is a battery.

6. The capsular endoscope according to claim 5, wherein the battery includes primary cells.

7. The capsular endoscope according to claim 6, wherein the battery includes secondary cells.

8. The capsular endoscope according to claim 1, wherein the power supply is a generation device.

9. The capsular endoscope according to claim 8, wherein the power supply is composed of fuel cells.

10. The capsular endoscope according to claim 1, wherein the power supply is a power receiving unit for receiving power externally fed by radio.

11. The capsular endoscope according to claim 1, wherein the power feeding means is a transformer, and a primary coil and a secondary coil of the transformer are disposed inside the first capsule case and the second capsule case, respectively.

* * * * *